United States Patent [19]

Spitz

[11] Patent Number: 4,600,557
[45] Date of Patent: Jul. 15, 1986

[54] SYSTEM FOR DEODORIZING AND DECONTAMINATING AUTOPSY ROOMS

[76] Inventor: Werner U. Spitz, 50 Stonehurst, Grosse Pointe Shores, Mich. 48236

[21] Appl. No.: 712,220

[22] Filed: Mar. 15, 1985

Related U.S. Application Data

[63] Continuation-in-part of Ser. No. 499,363, May 31, 1983, abandoned.

[51] Int. Cl.⁴ .............................................. A61L 9/00
[52] U.S. Cl. ......................................... 422/4; 52/138; 98/115.1; 422/5; 422/120; 422/168
[58] Field of Search ....................... 422/4, 5, 120, 168; 52/130-132, 138; 55/279; 98/115 R; 27/23

[56] References Cited

U.S. PATENT DOCUMENTS

| | | | |
|---|---|---|---|
| 1,002,223 | 9/1911 | Clayton | 52/131 X |
| 1,041,637 | 10/1912 | Lawrence | 52/130 |
| 3,337,455 | 8/1967 | Wilson et al. | 422/168 X |
| 3,721,067 | 3/1973 | Agnew | 422/4 X |
| 3,966,407 | 6/1976 | Zuckerberg et al. | 422/120 X |
| 4,553,992 | 11/1985 | Boissinot et al. | 422/121 X |

FOREIGN PATENT DOCUMENTS

| | | | |
|---|---|---|---|
| 2365070 | 7/1975 | Fed. Rep. of Germany | 422/4 |
| 7229098 | 9/1974 | France | 422/4 |

*Primary Examiner*—Barry S. Richman
*Assistant Examiner*—Brion P. Heaney
*Attorney, Agent, or Firm*—Barnes, Kisselle, Raisch, Choate, Whittemore & Hulbert

[57] ABSTRACT

A system for deodorizing and decontaminating autopsy rooms where autopsies are conducted on decomposed human remains wherein large amounts of noxious and malodorous gases are given off comprising an exhaust fan for removing large volumes of air and noxious gases substantially instantaneously from the specific autopsy environment and directing the air and noxious gases to a chamber, a burner associated with the chamber such that the flammable decomposition gases being exhausted are bombarded by a flame, ignited, burned and deodorized, and a duct associated with the chamber for directing the air and burned gases to the exterior of the building.

8 Claims, 2 Drawing Figures

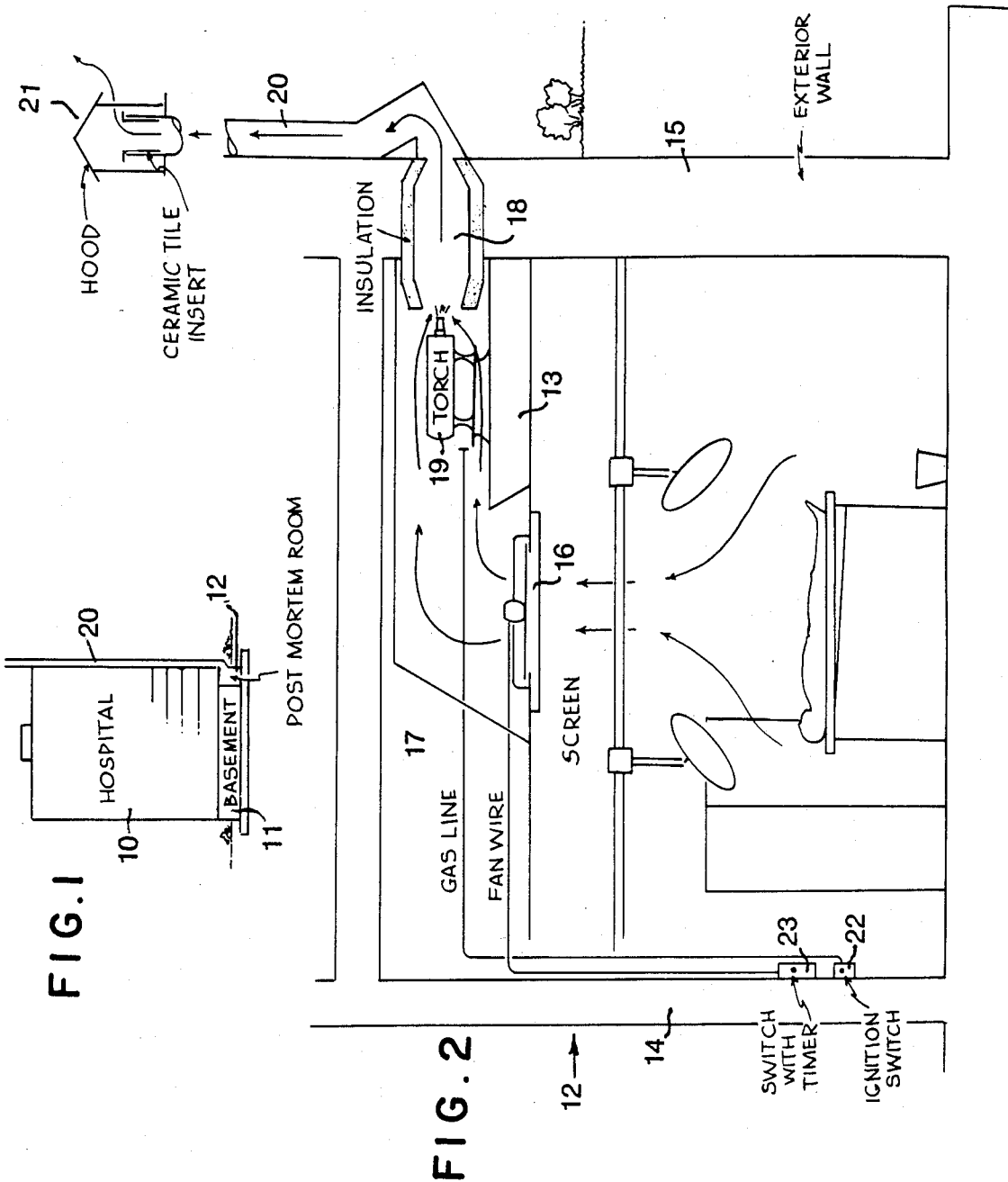

SYSTEM FOR DEODORIZING AND DECONTAMINATING AUTOPSY ROOMS

This application is a continuation-in-part of application Ser. No. 499,363 filed May 31, 1983 and now abandoned.

This invention relates to autopsy or postmortem rooms and particularly to the deodorizing and decontaminating of such rooms. Regular hospital autopsies do not necessarily involve decomposed bodies. But in most jurisdictions in the United States, in fact, in most areas of the world, medicolegal autopsies, i.e., coroner's and medical examiner's autopsies are conducted in departments of pathology of specially designated hospitals. My invention is particularly applicable to such institutions.

BACKGROUND AND SUMMARY OF THE INVENTION

Decomposing human remains generate noxious and malodorous odors which are probably among the most offensive known to man. These highly disagreeable odors affect not only those in the immediate area, but the smell rapidly permeates walls and spreads around doors and cracks, to the extent that it soon becomes noticeable in the entire wing of a building. Various methods to eliminate these odors are being used by hospitals, coroner's and medical examiner's offices, where such autopsies are conducted. However, no method to date is entirely effective.

These methods usually consists of complete air exchange, at a rapid rate, in the room in which the autopsy is performed. Two systems have been used. One utilizes an air system. Another provides airlocks. Both systems are costly and airlocks take up space.

However, there is not presently available a satisfactory low cost system to deodorize autopsy rooms in which decomposed remains are subjected to post-mortem examination. Autopsy rooms in older hospitals have no provisions for odor removal and resort to methods such as chemical deodorizers, which are ineffective and attempt to cover up one odor with another. In newer hospitals, attempts have been made to use air locks and equipment for rapid exchange of air. Neither is intended for autopsies on decomposed remains and is unable to control these odors, besides being expensive to install and maintain.

Clayton, U.S. Pat. No. 1,002,223 (1911) and Lawrence, U.S. Pat. No. 1,041,637 (1912) are concerned with long term preservation of a body after burial in a mausoleum. Such devices remove moisture from the casket containing the body by circulating dry air over the body. This process takes a long time, probably months, and changes the body into a leather-like mummy. This change produces artefacts and precludes adequate preservation of the surface of the body, which is of greatest concern to the forensic pathologist examining a body for possible injuries. The present invention is solely concerned with examination after recovery of an already decomposed body and does not alter or deteriorate the tissues in any way. It is essential that the system does not alter or deteriorate the tissues.

Wilson, U.S. Pat. No. 3,337,455 (1967) is directed to sewage lift stations. Sewage is introduced and withdrawn from a concrete tank and an incumbustible mixture of sewer gas and air is withdrawn through a pipe to a deodorizer, to a burner. Such an arrangement of a small pipe would be totally inadequate for handling the malodorous gases from an autopsy room. The intensity of the odor which emanates from decomposed remains, even before incision of the body, and the enormously rapid spread of this odor through the building preclude such a pipe system.

Agnew, U.S. Pat. No. 3,721,067 (1973) and Zuckerberg, U.S. Pat. No. 3,966,407 (1976) are directed to a different need. They are both concerned with sterilization of air, i.e., elimination of air-borne microorganisms from operating rooms. Neither is effective for odor control and for our purpose are entirely ineffective.

Kaplan, U.S. Pat. No. 3,880,096 (1975) is specifically designed for autopsy tables and provides for downward draft ventilation. However, a closer study of this method clearly indicates, that the downward draft will direct foul odors away from the pathologist performing the examination, but will not keep foul odors from spreading in the building.

The pathologist performing the autopsy is not the immediate concern. It is the entire hospital, the entire building in which such post-mortem examination is performed that is addressed by my invention.

Jewett, of New York, and Lipshaw, of Detroit, have both marketed this type of product and, whereas, it is moderately effective for odor control in the case of an autopsy of a fresh dead body in a hospital, or veterinary clinic, it is entirely unable to cope with the large volumes of gases which emanate under pressure from decomposed human remains, as is often the case in medicolegal settings.

Accordingly, among the objectives of the invention are to provide a system which will eliminate the odor from a contaminated autopsy room, deodorize and expel the air from the building; and which system is low in cost and easy to construct, operate and maintain.

In accordance with the invention, the method and system comprises withdrawing large volumes of noxious gases substantially instantaneously from the specific autopsy environment and directing the gases to a chamber where the flammable decomposition gases are bombarded by a flame, ignited, burned and deodorized, and the air and burned gases directed to the exterior of the building.

DESCRIPTION OF THE DRAWINGS

FIG. 1 is a diagrammatic view of a building embodying the invention.

FIG. 2 is a diagrammatic view of an enlarged scale of an autopsy room and a portion of a building embodying the invention.

DESCRIPTION

Referring to FIG. 1, in the preferred form, the invention comprises a building 10 having a basement 11 in which an autopsy or postmortem room 12 is located. As shown in FIG. 2, the room 12 includes a ceiling 13, interior walls 14 and an exterior wall 15. An exhaust fan 16 is located in the ceiling 13 for continuously withdrawing the air and the decomposition gases and directing them to a plenum 17 above the ceiling 13 and then to an insulated chamber 18 in the exterior wall 15. A continuous flame from ignition means such as a torch or burner 19 is directed into the chamber 18 and as the air mixes with the flame and is exposed to the turbulence of the flame, the flammable decomposition gases are bombarded by the flame, ignited, burned and deodorized. The system further includes a pipe or chimney 20 connected to chamber 18 and extending externally of the building to the top level with a hood 21 protecting the open end of the pipe 20 but the sides of the structure being open so that the air and burned gases flow freely to the atmosphere.

The putrefactive noxious or malodorous gases generated in a decomposing human body consist mainly of methane and are flammable. The autopsy room is best located in a basement or a one story part of the building. The exhaust ceiling fan 16, preferably 3' in diameter, is mounted inside a metal bonnet, with a course grid on the ceiling 13 to protect the blades. The fan pulls large amounts of the contaminated air substantially instantaneously from the region of the specific autopsy into the bonnet, passes it through a plenum 17 and into insulated chamber 18 which is large enough to accommodate the gas operated burner 19, but preferably not less than 18"×18". Inside the chamber 18 the flammable decomposition gases are bombarded by the flame, ignited, burnt and deodorized. The airflow then continues into pipe or chimney 20 with an interior diameter of 8". The pipe or chimney passes along the exterior of the building to above the roof. The difference in volume between the chamber 18 and the pipe or chimney 20 provides for slowing of the airflow through the chamber 18, allowing for more complete combustion of any flammable materials within the gases.

The burner and the fan are turned on by a single ignition-switch 22 connected to a timer 23. In this way the system can be started before the autopsy and continued until all odors are evacuated from the room.

It can thus be seen that the method and system are simple, easy to install, relatively inexpensive and adaptable to most situations.

Inasmuch as the decomposition gases consist primarily of methane, exposure to flame insures that the gases are burned. It should be understood that the air being passed through the chamber comprises normal room air and the decomposition gases and as a result the gases being burned do not necessarily form a continuous flame in the chamber 18.

The present invention enables a post-mortem examination to be conducted on a body in a state of advanced decomposition in a hospital, without spreading the offensive odor throughout the building. The system is low in cost and easy to construct, operate and maintain.

The system comprises withdrawing the air from the autopsy room and directing the air to a chamber where the flammable decomposition gases in the air are bombarded by a flame, ignited, burned, and deodorized. The air and burned gases are then directed to the exterior of the building.

The fundamental concept of my invention is the immediate 'lift up' or 'scooping out' of large volumes of malodorous gases from the area of autopsy. In fact, it is essential that the system, subject of our invention, be set in motion before the body is wheeled in to the room in order to start the rapid flow of air, i.e. the 'scooping action' and thus prevent any spread of gases laterally by directing all possible gases toward the ceiling, out of the area and out of the building by way of the incinerating chamber. For more effective odor control a timer continues the operation of the system for 1-2 hours after the autopsy has been completed and the body returned to storage.

In a typical example, the room has a size of about 10'×13'×10' high, two doors which are open, and air flow is at least 3700 cubic feet per minute.

I claim:

1. A method for deodorizing and decontaminating autopsy rooms wherein autopsies are conducted on decomposing human remains comprising:
   initiating withdrawal of large volumes of air and noxious gases substantially instantaneously from an autopsy room in a building prior to performing an autopsy;
   directing the large volume of air and noxious gases from said autopsy room to a chamber;
   subjecting the air and noxious gases withdrawn from said autopsy room to sufficient temperature within said chamber to thereby ignite, burn and deodorize flammable gases;
   directing the air and burned gases to the exterior of said building;
   performing an autopsy within said autopsy room while continuing the withdrawal of air and noxious gases from said autopsy room; and
   continuing the withdrawal of air and noxious gases from said autopsy room for a period of time after the completion of said autopsy.

2. The method set forth in claim 1 wherein said temperature is provided by a flame.

3. The method set forth in claim 2 wherein said flame functions continuously during the withdrawal of air and noxious gases from said autopsy room.

4. A system for deodorizing and decontaminating autopsy rooms wherein autopsies are conducted on decomposing human remains wherein large amounts of noxious and malodorous gases are given off comprising:
   an autopsy room in a building;
   a chamber;
   a plenum connecting said autopsy room with said chamber whereby said autopsy room is in fluid communication with said chamber;
   exhaust means for withdrawing large volumes of air and noxious gases substantially instantaneously from the specific autopsy environment and directing the gases to said plenum and into said chamber;
   ignition means associated with the chamber such that flammable decomposition gases within the volume of air and noxious gases being exhausted are bombarded by a flame, ignited, burned and deodorized; and
   duct means in fluid communication with said chamber for directing the air and burned gases to the exterior of said building.

5. The system set forth in claim 4 wherein said chamber is insulated.

6. The system set forth in claim 4 including control means for controlling the operation of said exhaust means.

7. The system set forth in claim 4 including control means for controlling the operation of said ignition means.

8. The system set forth in claim 4 wherein said autopsy room is at the lowest level of said building and said duct means extends from said chamber externally of said building to the upper levels of said building.

* * * * *